United States Patent
Ulrich et al.

(10) Patent No.: US 6,767,557 B2
(45) Date of Patent: Jul. 27, 2004

(54) TASTE MASKED PHARMACEUTICAL COMPOSITIONS

(75) Inventors: Stephen A. Ulrich, Cherry Hill, NJ (US); Karen R. Zimm, Stockton, NJ (US)

(73) Assignee: Ortho-McNeil Pharmaceutical, Inc., Raitan, NJ (US)

(*) Notice: Subject to any disclaimer, the term of this patent is extended or adjusted under 35 U.S.C. 154(b) by 57 days.

(21) Appl. No.: 10/083,775

(22) Filed: Feb. 26, 2002

(65) Prior Publication Data

US 2002/0197327 A1 Dec. 26, 2002

Related U.S. Application Data

(60) Provisional application No. 60/273,473, filed on Mar. 5, 2001.

(51) Int. Cl.[7] .................................................. A61K 9/14
(52) U.S. Cl. ........................................ 424/497; 514/974
(58) Field of Search ................................. 424/464, 465, 424/489, 490, 494, 497, 441, 435

(56) References Cited

U.S. PATENT DOCUMENTS

| 5,489,436 A | 2/1996 | Hoy et al. |
| 5,599,556 A | 2/1997 | Meyer et al. |
| 6,136,347 A | 10/2000 | Pöllinger et al. |
| 6,328,994 B1 * | 12/2001 | Shimizu et al. ............. 424/489 |
| 6,555,124 B1 * | 4/2003 | Kolter et al. ............... 424/434 |

FOREIGN PATENT DOCUMENTS

| WO | WO 00/06122 A1 | 2/2000 |
| WO | WO 00/76479 A1 | 12/2000 |
| WO | WO 01/87269 A1 | 11/2001 |

OTHER PUBLICATIONS

Harder, S. et al.; Ciprofloxacin absorption in different regions of the human gastrointestinal tract. Investigations with the hf–capsule; Br. J. Clin. Pharmac. (1990), 30, 35–39.

International PCT Search Report for Application No. PCT/US02/05795 dated Nov. 12, 2002.

* cited by examiner

*Primary Examiner*—James M. Spear

(57) ABSTRACT

A taste masked pharmaceutical composition comprising a microcapsule, wherein the microcapsule comprises a pharmaceutically active agent core coated with a taste masking effective amount of a water-insoluble enteric coating, wherein the coating comprises a weakly acidic methacrylic acid-ethyl acrylate copolymer.

12 Claims, No Drawings

TASTE MASKED PHARMACEUTICAL COMPOSITIONS

CROSS REFERENCE TO RELATED APPLICATIONS

This application claims benefit of provisional application Serial No. 60/273,473, filed Mar. 5, 2001, which is incorporated by reference herein.

FIELD OF THE INVENTION

The present invention relates to novel taste masked pharmaceutical compositions. More particularly, this invention relates to taste masked pharmaceutical compositions comprising microcapsules for reconstitution with a liquid vehicle for oral administration, which effectively mask the taste of pharmaceuticals or nutritional supplements that have a bitter or otherwise undesirable taste characteristic.

BACKGROUND OF THE INVENTION

Pharmaceutically active agents can be administered to the patient in many forms with oral administration being the most popular. Active agents can be given to the patient orally as liquid solutions, emulsions, suspensions or in solid form such as capsules or tablets. Infants, children, older persons and many other persons are unable to swallow whole tablets and capsules. Therefore, in cases where the dosage to be administered cannot be made into a very small tablet or capsule, it is desirable to provide the medicine in liquid or chewable form, direct administration as a powder or granules in suspension would also be advantageous.

Many active ingredients, such as antibiotics, possess a strong, unpleasant taste. In particular, unpleasant-tasting active ingredients include gyrase inhibitors; particularly, those of the naphthyridone-carboxylic acid and quinolone-carboxylic acid types; more particularly, those selected from levofloxacin, ciprofloxacin, norfloxacin, ofloxacin or enoxacin.

When an active agent is formulated as a tablet or capsule intended to be swallowed whole, the taste of the active ingredient is usually not an issue since the capsule keeps the active ingredient from contacting the mouth and the tablet can be coated to prevent contact of the active with the mouth for the short time the tablet is present in the mouth. In contrast, masking of the unpleasant taste characteristics of the active agent is an extremely important factor in the formulation of liquid and chewable pharmaceuticals. The palatability of the liquid or chewable dosage form is a critical factor in ensuring patient compliance.

In some cases, the unpleasant taste of the active agent in a liquid or chewable formulation can be overpowered by adding flavoring ingredients and sweeteners to improve taste and palatability. However, where the active agent possesses a particularly strong or bitter taste, such as is the case with many antibiotics, the mere addition of such flavoring ingredients and sweeteners is insufficient to improve taste and palatability. Accordingly, various taste masked coating compositions have been employed in the formulation of liquid suspension and chewable tablet dosage forms.

Besides a complete concealment of the taste, a rapid and complete release is critical for the beneficial effects of an active ingredient to be made available to a patient. The composition, though, must also preserve the stability of the active ingredient in a humid environment prior to use. For a coated granule composition to ensure bioavailability that is equivalent to a tablet formulation, the coating must be formulated to release the active ingredient in an appropriate environment.

For example, it is known for numerous active ingredients that there is an absorption window in the upper small intestine and that absorption in the lower intestine is greatly reduced (S. Harder, U. Fuhr, D. Beermann, A. H. Staib, Br. J. Clin. Pharmac., 1990, 30, 35). In elderly people, there are also frequently occurring deviations of the gastric pH in the direction of a hypoacidic medium. In an attempt to ensure bioavailability, therefore, certain water-insoluble coated formulations (using a "reverse enteric coating") have been designed to dissolve in a weakly acidic medium such as one having a pH 4.5, for example, the acidic environment of the stomach. We have discovered that the use of a reverse enteric coating formulation, however, does not result in reproducible bioavailability to all patients due to the physical variability among patients in passage of a reverse enteric coating formulation through the gastrointestinal tract.

U.S. Pat. No. 5,599,556 discloses liquid formulations where the active ingredient is coated with a single outer polymeric coating derived from prolamine cereal grain proteins and a plasticizing agent. The coatings are designed to rapidly degrade once the composition leaves the mouth.

U.S. Pat. No. 5,489,436 discloses chewable tablets made from a coated medicament where the coating is a "reverse enteric coating" designed to be soluble at the acidic pH of the stomach but relatively insoluble in the mouth. The coatings comprise a polymer blend of dimethylaminoethyl methacrylate and neutral methacrylic acid ester and a cellulose ester.

U.S. Pat. No. 6,136,347 discloses taste-masked microcapsules for use in liquid suspension formulations, particularly in oil-based juices or a suitable liquid such as water. The microcapsule comprises an active ingredient granule coated with a single outer polymeric coating derived from film-forming agents such as neutral methyl and ester compounds of polymethacrylic acid. The coatings are designed to be water-insoluble and rapidly degrade once the composition reaches the acidic environment of the stomach.

There is thus a need for a water-insoluble taste masked composition which is stable, bioavailable and retains its coating integrity and, thereby, its taste masking properties in an aqueous, pH-neutral or pH-acidic environment over an extended period, yet which exhibits immediate bioavailability after passage into the intestine.

An object of the present invention is to provide taste masked pharmaceutical compositions. An object of the present invention is to provide taste masked pharmaceutical compositions comprising microcapsules, for reconstitution with a liquid vehicle for oral administration.

SUMMARY OF THE INVENTION

The present invention provides taste masked pharmaceutical compositions comprising a microcapsule, wherein the microcapsule comprises a pharmaceutically active agent core coated with a taste masking effective amount of a water-insoluble enteric coating, wherein the coating comprises a weakly acidic methacrylic acid-ethyl acrylate copolymer.

An embodiment of the invention is a taste masked pharmaceutical composition wherein the pharmaceutically active agent is an antibiotic drug.

Another embodiment of the invention is a taste masked pharmaceutical composition wherein the antibiotic drug is selected from levofloxacin.

An embodiment of the invention also includes a method for reconstituting a taste masked pharmaceutical composition according to the invention in a liquid vehicle such as an oily juice for oral administration.

DETAILED DESCRIPTION OF THE INVENTION

The present invention provides taste masked pharmaceutical compositions comprising microcapsules, wherein the microcapsules comprise a pharmaceutically active agent coated with a taste masking effective amount of a water-insoluble enteric coating, wherein the coating comprises a weakly acidic methacrylic acid-ethyl acrylate copolymer.

The invention relates in particular to a taste masked pharmaceutical composition comprising a pharmaceutically active agent having an unpleasant taste that is coated with an enteric coating. Enteric coatings are those that are insoluble at the acidic pH levels of the stomach and are soluble in the basic pH of the intestine. The coatings provide a protective layer which masks the unpleasant taste characteristics of the active ingredient while passing through the mouth and which remains stable in the acid environment of the stomach because of its low solubility therein, but is readily soluble in the intestine and, thereby, provides immediate release of the active agent in the intestine. The enteric coatings encapsulate the active ingredient, effectively and stably masking the taste of the active agent while providing reproducible bioavailability to a varied patient population.

The taste masked pharmaceutical composition of the present invention utilizes an enteric coating which is weakly acidic, soluble in the basic pH of the intestine, generally above a pH of about 5.5, preferably above about 6.0. The coatings provide for rapid release and absorption of the drug, which is generally desirable in the case of liquid dosage forms.

In an embodiment of a taste masked composition of the present invention, the pharmaceutically active agent is an antibiotic drug selected from those of the naphthyridone-carboxylic acid type or quinolone-carboxylic acid type; particularly levofloxacin, ciprofloxacin, norfloxacin, ofloxacin, enoxacin or other related quinolone antibiotics, as well as other known antibiotics which have an unpleasant taste and are formulated for oral liquid administration such as cephalosporins, macrolide antibiotics, penicillins and the like. Other active agents which may be beneficially employed in the compositions of the invention include analgesic drugs, such as tramadol or codeine, anti-inflammatory drugs such as ibuprofen, naproxen and other NSAID's (non-steroidal antiinflammatory drugs). Other active agents for which the compositions of the invention may be employed include drugs for delivery to the intestinal tract, including, but not limited to, antihistamines, antibacterials, antimicrobials, decongestants, antidepressants, anti-psychotics, antivirals, oncolytics, vaccines, antiepileptics such as topiramate, anti-asthma compounds, antispasmodics and the like.

An embodiment of this invention includes a taste masked pharmaceutical composition for oral administration wherein the antibiotic is levofloxacin coated with a taste masking effective amount of a water-insoluble enteric coating comprising a weakly acidic methacrylic acid-ethyl acrylate copolymer. Levofloxacin (marketed under the tradename LEVAQUIN®) is the INN (International Nonproprietary Name) for a compound having the CAS (Chemical Abstracts Society) Registry Number: 100986-85-4 and the CAS Index Name: (3S)-9-fluoro-2,3-dihydro-3-methyl-10-(4-methyl-1-piperazinyl)-7-oxo-7H-pyrido[1,2,3-de]-1,4-benzoxazine-6-carboxylic acid.

The pharmaceutically active agent is present in the composition in a therapeutically effective amount, which amounts produce the desired therapeutic response upon oral administration and can be readily determined by one skilled in the art. In determining such amounts, the particular compound being administered, the bioavailability characteristics of the agent, the dose regimen, the age and weight of the patient and other factors must be considered.

In an embodiment of the present composition, the therapeutically effective amount of the antibiotic levofloxacin is present in a range of from about 1 gram to about 5 grams of levofloxacin per 100 mL of a reconstituted composition. In another embodiment of the present composition, the therapeutically effective amount ranges from about 2.5 grams to about 5 grams of levofloxacin per 100 mL of a reconstituted composition. In a further embodiment of the present composition, the therapeutically effective amount is selected from about 1 gram of levofloxacin per 100 mL of a reconstituted composition, about 2.5 grams of levofloxacin per 100 mL of a reconstituted composition or about 5 grams of levofloxacin per 100 mL of a reconstituted composition.

In accordance with the invention, the active agent is generally spray coated with a MAE copolymer coating (either directly or after granulation) and then the coated agent is admixed with other pharmaceutically acceptable additives such as sweeteners or flavorings and the like.

In accordance with the invention, there is provided a taste masked pharmaceutically active agent comprising a core of active agent, optionally associated with inactive pharmaceutical adjuvants; the core being coated with a taste masking effective amount of a water-insoluble enteric coating comprising a weakly acidic MAE (methacrylic acid-ethyl acrylate) copolymer.

The taste masked active agent is provided for reconstitution with a liquid vehicle for oral administration as a liquid pharmaceutical composition such as a solution, emulsion or suspension, having an acidic pH less than about 5.5.

The details of the enteric coating used on the pharmaceutically active agent and the coating techniques thereof are herein described. The diffusion and solubility of the coating depends on the physicochemical properties of the copolymer coating and the drug being coated. The copolymer coating used in the present invention provides the desired diffusion, stability and release characteristics. That is, the coating provides the appropriate taste masking while present in the mouth and insolubility in the stomach but immediate disintegration and diffusion of the active agent when present at the basic pH levels of the intestine. The diffusion characteristics thus obtained provide the appropriate immediate bioavailability of the active agent as is generally desirable in a liquid composition.

According to techniques known to one skilled in the art, the particles of active agent may be milled, particularly if the particles are irregularly shaped and sized. The milled or unmilled active agent is then granulated prior to coating. Preferably, the active agent cores to be coated will be in the range of about 3 to about 500 microns.

The optimum thickness of the coating material applied to the active agent core will depend on the physicochemical characteristics of the active agent and the taste masking effective amount of the coating. In an embodiment of the invention, a taste masking effective amount of the coating is a weight ratio of coating weight to weight of the active agent in a range of from about 0.5 to about 1.5 or from about 1.5 to about 0.5. An embodiment of the invention includes a taste masking effective amount of the coating wherein the weight ratio of coating weight to weight of the active agent is in a range of from about 0.75 to about 1.25 or from about 1.25 to about 0.75. An embodiment of the invention also includes a taste masking effective amount of the coating wherein the weight ratio of coating weight to weight of the active agent is a weight ratio of about 1.0 to about 1.0.

The ingredients for the copolymer coating used in the present taste masked composition are as disclosed herein. The preferred MAE copolymer is selected from the copolymer blends sold under the tradename KOLLICOAT® MAE 30 DP or KOLLICOAT® MAE 100 P, preferably KOLLICOAT® MAE 30 DP. The MAE copolymer coating is a weakly acidic, anionic copolymer derived from methacrylate acid-ethyl acrylate with a mean molecular weight of 250,000. The preferred MAE copolymer is designed to be soluble in the basic pH of the intestine, generally above a pH of about 5.5, preferably above a pH of about 6.0 and insoluble in a liquid vehicle such as one used for reconstitution having an acidic pH less than about 5.5.

Other optional additives may be added to the copolymer coating, including suitable plasticizers or gloss intensifiers (such as 1,2-propylene glycol, triethyl citrate, polyethylene glycols or triacetin), anti-foaming agents (such as a silicone antifoam), excipients (such as talc, Syloid, Aerosil, Kaolin or pigments) or a polyvinylpyrrolidone or 2-vinyl-pyridine (V)/styrene(S) copolymer.

The preparation of the composition may be accomplished by a variety of coating techniques known in the art including spray coating and wet granulation techniques. Preferably, a Glatt GPCG 1 unit with rotor insert is used to apply the coating. Generally, the MAE coating material is dissolved in water to make a solution. The water is removed in the drying process and is thus not present in the final composition. The total copolymer concentration in the coating solutions can vary, generally in the range of about 5 to about 30% by weight (w/w); and preferably, the total copolymer concentration in the coating solution is about 17.55% w/w.

Once the dried coated cores are obtained, the coated cores are optionally admixed with pharmaceutically acceptable adjuvants such as pH stabilizers, acidifying agents, preservatives, coloring agents and optional sweetening agents, debittering agents, flavoring agents or mixtures thereof. A preparation for oral administration can then be formed as a liquid suspension or as a powder for reconstitution with a liquid vehicle by the pharmacist prior to dispensing.

Optional sweetening agents include, but are not limited to, sugar sweeteners such as monosaccharides, disaccharides and polysaccharides. Examples of suitable sugar sweeteners include but are not limited to xylose, ribose, glucose, mannose, galactose, fructose, dextrose, sucrose, maltose, partially hydrolyzed starch or corn syrup solids and sugar alcohols such as sorbitol, xylitol, mannitol, glycerin and combination thereof. Preferably, the type of glycerin used is U.S.P. grade. The amount of sugar sweetener used in the composition will vary depending on the degree of sweetening desired for the particular composition. Generally the total amount of sugar sweetener used will be in the range of from 0 to about 100 grams per 100 mL of the composition. Preferably, the amount of sugar sweetener used will be in the range of from about 0 grams to about 10 grams per 100 mL of composition. More preferably, the amount of sugar sweetener used will be in the range of from about 2 grams to about 3 grams per 100 mL of composition.

Artificial sweeteners may be optionally employed in place of or in addition to sugar sweeteners as the sweetening agent. Preferably, a taste-masking composition comprises an artificial sweetener as the sweetening agent including, but not limited to, aspartame, sucralose, cyclamates, saccharin, acesulfame K or mixtures thereof. Preferably, the artificial sweetener is sucralose. The amount of artificial sweetener used in the composition will vary depending on the degree of sweetening desired for the particular composition. The amount of artificial sweetener used in the composition may vary from in the range of from about 0.45 to about 1.7 grams per 100 mL of composition. Preferably, the amount of artificial sweetener used is in the range of about 1 gram per 100 mL of composition.

In other embodiments of the present invention, a debittering agent may be optionally employed in addition to a sweetening agent and a flavoring agent. Debittering agents include, and are not limited to, natural debittering agents, artificial debittering agents or debittering agents which inhibit a chemosensory response in the mouth or nose or mixtures thereof. Debittering agents for use in the present invention are commercially available, such as those marketed under the names Prosweet FL N&A K (by Virginia Dare), Bitterness Modifier 36734 (by Bush, Boake and Allen, Inc.), Natural Taste Masker 501.441/A and Special Taste Masker Compound 501.437/A (by Firmenich, Inc.), and may be identified by those skilled in the art.

Optional flavoring agents added to the mixture should be of the type and amount desired for the particular suspension to meet the preferences dictated by the intended consumer of such suspension such as an adult or pediatric patient. Suitable flavoring agents include natural flavors, natural fruit flavors, artificial flavors, artificial fruit flavors, flavor enhancers or mixtures thereof. Natural flavors, artificial flavors or mixtures thereof include, and are not limited to, mint (such as peppermint or spearmint), menthol, cinnamon, vanilla, artificial vanilla, chocolate, artificial chocolate or bubblegum. Natural fruit flavors, artificial fruit flavors or mixtures thereof include, and are not limited to, cherry, grape, orange, strawberry or lemon. Flavor enhancers include, and are not limited to, citric acid. Flavoring agents are generally provided as a minor component of the formulation in amounts effective to provide a palatable flavor to the formulation. Flavoring agents are generally present in the formulation in amounts in the range of from about 0.02 to about 0.06 grams per 100 mL of the formulation. Preferably, flavoring agents are present in an amount in the range of about 0.04 grams per 100 mL of the formulation.

The formulation may contain pH stabilizers such as citric acid, added to the formulation to stabilize the pH of the formulation and prevent microbial growth. Citric acid is advantageously added since a lower pH will prevent microbial growth and add to the stability of the product.

It is also desirable to include an acidifying agent to the formulation of the present invention to maintain the integrity of the enteric taste masked coating and to stabilize the pH after reconstitution to enhance the effect of a preservative. The acidifying agents that are applicable for use in the present invention are those which are acidic in a liquid vehicle and are capable of lowering and maintaining the pH of the liquid vehicle below about a pH 5.0. The acidifying agent includes, and is not limited to, citric acid, sodium ascorbate or ascorbic acid. In the case of the present formulation, citric acid is preferred. One or more of such acidifying agents may be used in an amount to lower the pH of a reconstituted formulation to below about pH 5.0.

Preservatives useful in the present invention include but are not limited to sodium benzoate, potassium sorbate, salts of edetate (also known as salts of ethylenediaminetetraacetic acid, or EDTA, such as disodium edetate), parabens (such as methyl, ethyl, propyl and butyl p-hydroxybenzoic acids esters or mixtures thereof) or mixtures thereof. The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art. Sodium benzoate, propylparaben, butylparaben or mixtures thereof are preferred preservative ingredients and may be added to a pharmaceutical formulation containing levofloxacin although other pharmaceutically acceptable preservatives may be substituted therefor.

Preservatives are optionally present in amounts of up to about 1 gram per 100 mL of the formulation of the invention. In an embodiment of the invention, an individual preservative may be present in an amount in the range of from about 0 to about 0.5 gram per 100 mL of the formulation.

Coloring agents also may be incorporated in the formulation to provide an appealing color to the reconstituted formulation. The coloring agents should be selected to avoid chemical incompatibilities the other ingredients in the formulation. Suitable coloring agents for use in a pharmaceutical formulation are well known to those skilled in the art.

As stated, the taste masking formulations of the present invention satisfy the unique requirements of a reconstituted liquid formulation. In accordance with the invention, there is provided a formulation which is stable: the taste masking properties are maintained in a liquid vehicle after reconstitution for at least the duration of the treatment period (in the case of antibiotics, 7–14 days), while still providing appropriate taste masking when the product is administered.

In order to further illustrate the present invention and the advantages thereof, the following specific examples are given, it being understood that these examples are intended only to be illustrations without serving as a limitation on the scope of the present invention.

EXAMPLE 1

Taste Masked Levofloxacin Composition

Example 1 describes ranges for the components used in embodiments of the present invention:

EXAMPLE 1

Quantitative Composition of Coated Levofloxacin Cores

| Component | Range (mg) |
|---|---|
| Levofloxacin Hemihydrate | 3–257 |
| Hydroxypropyl Methylcellulose | 1.0–10.0 |
| Purified Water[a] | 50–250 |
| Methacrylic Acid Copolymer | 50–375 |
| Propylene Glycol | 10–50 |
| Purified Water[a] | 1.0–8.0 |

[a]Water removed after processing

EXAMPLE 2

Taste Masking Composition

The table in Example 2 lists the components in a formulation of the invention, wherein the active agent core weight of about 250 mg and a 17.55% w/w coating solution, comprising a MAE copolymer weight of about 250 mg, a water weight of about 4 mg and a polypropylene glycol plasticizer weight of about 40 mg, corresponds to about a 1:1 weight ratio of MAE:coated core.

EXAMPLE 2

Quantitative Composition of Coated Levofloxacin Cores

| Component | Amount (mg) |
|---|---|
| Levofloxacin Hemihydrate | 256.15 |
| Hydroxypropyl Methylcellulose | 3.8422 |
| Purified Water[a] | 124.23 |
| Methacrylic Acid Copolymer | 259.989 |
| Propylene Glycol | 39.0089 |
| Purified Water[a] | 3.98 |

[a]Water removed after processing

EXAMPLE 3

Manufacturing Procedure for a Taste Masked Levofloxacin Acid Stable Coated Core

A taste masked levofloxacin acid stable coated core was prepared as follows:

Weighing and Milling
1. Weigh the ingredients listed in Example 2.
2. Mill the pure drug substance with an appropriate mill.

Binder Solution Preparation

Combine the purified water and the hydroxypropyl methyl cellulose powder in a stainless steel tank and mix well until hydrated.

Coating Solution Preparation
1. Weigh the propylene glycol, purified water and the MAE material.
2. Add the propylene glycol to the purified water and mix.
3. Add the MAE to the previous mixture and continue mixing with a suitable mixer. Mix for 10–20 minutes until all is dispersed.
4. Reduce the mixer speed and continue mixing if needed.

Rotor Granulation
1. Place the milled levofloxacin hemihydrate into a Glatt GPCG 1 Rotor Granulator.
2. Set the appropriate processing parameters listed in Table 1. Adjust these parameters as needed during processing.
3. Spray the amount of hydroxypropyl methylcellulose binder solution to make fine small granules.
4. Dry the granules and discharge for further processing.

Rotor Coating Directions
1. Weigh the appropriate amount of coating solution for the Acid Stable Coat in an appropriate container.
2. Assemble the rotor or continue from Rotor Granulation Step 2 using the appropriate parameters and equipment as shown in Table 1.
3. Begin spraying the MAE solution.
4. Maintain a product temperature at about 40° C.
5. Discharge the coated cores into fiber drum(s) lined with polyethylene bags and weigh on an appropriate scale to determine the yield.

Table 1 summarizes the coating parameters for the batch.

TABLE 1

Coating Parameters for Coated Levofloxacin Beads Manufactured Using a Glatt GPCG-1 Coater with a Rotor Insert

| | |
|---|---|
| Batch Size (kg) | 4.3 |
| Inlet Temperature During Spraying (° C.) | 67–75 |
| Product Temperature During Spraying (° C.) | 41–50 |
| Exhaust Temperature During Spraying (° C.) | 39–49 |

TABLE 1-continued

Coating Parameters for Coated Levofloxacin Beads Manufactured
Using a Glatt GPCG-1 Coater with a Rotor Insert

| | |
|---|---|
| Nozzle Size (mm) | 1.2 |
| Atomization Air (bar) | 1–3 |
| Air Velocity (m/sec) | 4.5–5.5 |
| Rotor Speed (rpm) | 1080 |
| Spray Rate (g/min) | 16–18.4 |
| Spray Time (min) | 300 |
| Drying Time (min) | 2–15 |
| Product Drying Temp (° C.) | 68–70 |

EXAMPLE 4

Taste Masked Levofloxacin Composition

Following coating of the levofloxacin cores, embodiments of the present invention include a formulation wherein the coated cores are admixed with an excipient powder with the ranges of components shown in Example 4:

EXAMPLE 4

Quantitative Composition of Excipient Blend Powder for Use with
Coated Levofloxacin for Reconstitution
(250 mg/5 mL when Reconstituted)

| Component | Range (gms) |
|---|---|
| Microcrystalline Cellulose and Carboxymethyl Cellulose, NA NF | 0.05–0.50 |
| Sucrose, NF | 0.5–5.0 |
| N&A Fruit Punch Flavor | 0–0.5 |
| FD&C Red #40 | 0–0.1 |
| Citric Acid, Anhydrous USP | 0.005–1.0 |
| Benzoic Acid | 0.001–0.1 |
| Xanthan Gum USP, EP, JPE | 0.001–0.0 |
| Sucralose NF (pure substance, not marketed powder)) | 0.05–0.10 |

EXAMPLE 5

Taste Masked Levofloxacin Composition

Following coating of the levofloxacin cores, embodiments of the present invention include a formulation wherein the coated cores are admixed with an oily juice with the ranges of components shown in Example 5:

EXAMPLE 5

Quantitative Composition of Non-Aqueous Diluent for Use with
Coated Levofloxacin for Reconstitution
(250 mg/5 mL when Reconstituted)

| Component | % W/W |
|---|---|
| Lecithin (soybean lecithin or equivalent) | 0.05–2.5 |
| Confectioner's Sugar NF | 10–90 |
| Peppermint Flavor | 0.01–0.5 |
| Medium Chain Triglycerides | 20–70 |

EXAMPLE 6

Taste Masked Levofloxacin Composition

Following coating of the levofloxacin cores, an embodiment of the present invention is a formulation wherein the coated cores are admixed with an excipient powder with the components shown in Example 6:

EXAMPLE 6

Quantitative Composition of Excipient Blend Powder for Use with
Coated Levofloxacin for Reconstitution
(250 mg/5 mL when Reconstituted)

| Component | Amount (gms) |
|---|---|
| Microcrystalline Cellulose and Carboxymethyl Cellulose, NA NF | 0.275 |
| Sucrose, NF | 2.5 |
| N&A Fruit Punch Flavor | 0.0075 |
| FD&C Red #40 | 0.002 |
| Citric Acid, Anhydrous USP | 0.025 |
| Benzoic Acid | 0.005 |
| Xanthan Gum USP, EP, JPE | 0.005 |
| Sucralose NF (pure substance, not marketed powder)) | 0.051 |

EXAMPLE 7

Taste Masked Levofloxacin Composition

Following coating of the levofloxacin cores, an embodiment of the present invention is a formulation wherein the coated cores are admixed with an oily juice with the ranges of components shown in Example 7:

EXAMPLE 7

Quantitative Composition of Non-Aqueous Diluent for Use with
Coated Levofloxacin for Reconstitution
(250 mg/5 mL when Reconstituted)

| Component | % W/W |
|---|---|
| Lecithin (soybean lecithin or equivalent) | 1.0 |
| Confectioner's Sugar NF | 55.0 |
| Peppermint Flavor | 0.03 |
| Medium Chain Triglycerides | 43.97 |

EXAMPLE 8

Taste Masked Levofloxacin Composition

An embodiment of the present invention includes a formulation with the composition shown in the table of Example 8 to form a reconstituted liquid suspension for oral administration suitable for pediatric or adult use.

EXAMPLE 8

Quantitative Composition of Levofloxacin Powder for Reconstitution
with Water (250 mg/5 mL when Reconstituted)

| Component | g/5 mL |
|---|---|
| Levofloxacin Hemihydrate | 0.256[a] |
| Hydroxypropyl Methylcellulose | 0.004[a] |
| Purified Water USP, NF (for hydroxypropyl methylcellulose binder evaporated during process as a 3% w/w solution) | — |
| Methacrylic Acid Copolymer | 0.260[a] |
| Microcrystalline Cellulose and Carboxymethyl Cellulose, NA NF | 0.275 |
| Sucrose, NF | 2.5 |
| N&A Fruit Punch Flavor | 0.0075 |
| FD&C Red #40 | 0.002 |
| Citric Acid, Anhydrous USP | 0.025 |
| Benzoic Acid | 0.005 |
| Sucralose NF (pure substance, not marketed powder) | 0.051 |
| Propylene Glycol USP | 0.039 |

EXAMPLE 8-continued

Quantitative Composition of Levofloxacin Powder for Reconstitution with Water (250 mg/5 mL when Reconstituted)

| Component | g/5 mL |
|---|---|
| Xanthan Gum USP, EP, JPE | 0.005 |
| Water qs ad | 5.0 mL[b] |

[a]Based on theoretical coating level of 100% initial. Actual amount depends on the assay potency of the coated levofloxacin beads used in the batch.
[b]Water to be added by pharmacist before dispensing.

What is claimed is:

1. A taste masked pharmaceutical composition comprising a microcapsule, said microcapsule comprising a pharmaceutically active agent core coated with a taste masking effective amount of a water-insoluble enteric coating, wherein said pharmaceutically active agent is an antibiotic drug selected from a naphthyridone-carboxylic acid antibiotic or a quinolone-carboxylic acid antibiotic, and wherein the coating comprises a weakly acidic methacrylic acid-ethyl acrylate copolymer.

2. The formulation of claim 1 wherein the antibiotic drug is selected from levofloxacin, ciprofloxacin, norfloxacin, ofloxacin or enoxacin.

3. The formulation of claim 2 wherein the antibiotic drug is levofloxacin.

4. The formulation of claim 3 wherein levofloxacin is present in a range of from about 1 gram to about 5 grams of levofloxacin per 100 mL of a reconstituted formulation.

5. The formulation of claim 4 wherein levofloxacin is present in a range of from about 2.5 grams to about 5 grams of levofloxacin per 100 mL of a reconstituted formulation.

6. The formulation of claim 4 wherein levofloxacin is present in a range selected from about 1 gram of levofloxacin per 100 mL of a reconstituted formulation, from about 2.5 grams of levofloxacin per 100 mL of a reconstituted formulation or from about 5 grams of levofloxacin per 100 mL of a reconstituted formulation.

7. The formulation of claim 1 wherein the taste masking effective amount of the coating is a weight ratio of coating weight to weight of the active agent in a range of from about 0.5 to about 1.5 or from about 1.5 to about 0.5.

8. The formulation of claim 1 wherein the taste masking effective amount of the coating is a weight ratio of coating weight to weight of the active agent in a range of from about 0.75 to about 1.25 or from about 1.25 to about 0.75.

9. The formulation of claim 1 wherein the taste masking effective amount of the coating is a weight ratio of coating weight to weight of the active agent of about 1.0 to about 1.0.

10. The formulation of claim 1 wherein the weakly acidic methacrylic acid-ethyl acrylate copolymer is selected from a copolymer designed to dissolve at a pH greater than about pH 5.5.

11. The formulation of claim 10 wherein the methacrylic acid-ethyl acrylate copolymer is a copolymer designed to dissolve at a pH range of from about pH 5.5 to about pH 8.

12. The formulation of claim 1 wherein the active agent is levofloxacin: wherein the weakly acidic methacrylic acid-ethyl acrylate copolymer is a copolymer designed to dissolve at a pH range of from about pH 5.5 to about pH 8: and, wherein the taste masking effective amount of the coating is a weight ratio of coating weight to weight of levofloxacin of about 1.0 to about 1.0.

\* \* \* \* \*